US012612667B1

(12) United States Patent
Podlevsky et al.

(10) Patent No.: US 12,612,667 B1
(45) Date of Patent: Apr. 28, 2026

(54) SOLID PHASE RECOMBINASE POLYMERASE AMPLIFICATION FOR HUMAN PATHOGEN IDENTIFICATION

(71) Applicants: National Technology & Engineering Solutions of Sandia, LLC, Albuquerque, NM (US); Resonantia Diagnostics, Inc., Dallas, TX (US)

(72) Inventors: Joshua Podlevsky, Albuquerque, NM (US); Darren W. Branch, Albuquerque, NM (US); Adam Bolotsky, Albuquerque, NM (US); Matthew Jones, Dallas, TX (US)

(73) Assignees: National Technology & Engineering Solutions of Sandia, LLC, Albuquerque, NM (US); Resonantia Diagnostics, Inc., Dallas, TX (US)

( * ) Notice: Subject to any disclaimer, the term of this patent is extended or adjusted under 35 U.S.C. 154(b) by 462 days.

(21) Appl. No.: 18/141,514

(22) Filed: May 1, 2023

(51) Int. Cl.
*C12Q 1/68* (2018.01)
*C12Q 1/686* (2018.01)
*C12Q 1/6888* (2018.01)

(52) U.S. Cl.
CPC ........... *C12Q 1/6888* (2013.01); *C12Q 1/686* (2013.01)

(58) Field of Classification Search
CPC ...................................................... C12A 1/68
See application file for complete search history.

(56) References Cited

U.S. PATENT DOCUMENTS

| | | | |
|---|---|---|---|
| 10,272,434 B2 | 4/2019 | Khattak et al. | |
| 10,538,760 B2 | 1/2020 | Piepenburg et al. | |
| 11,634,765 B2 * | 4/2023 | Boutell | C12Q 1/6874 506/2 |
| 2017/0096648 A1 * | 4/2017 | Mazur | C12N 9/1252 |
| 2020/0087709 A1 | 3/2020 | Bracht et al. | |
| 2022/0112547 A1 * | 4/2022 | Armes | G01N 33/68 |
| 2022/0259648 A1 * | 8/2022 | Witters | C12Q 1/6869 |
| 2025/0269368 A1 * | 8/2025 | Reed | C12Q 1/6869 |

FOREIGN PATENT DOCUMENTS

| | | |
|---|---|---|
| WO | 2007096702 A2 | 8/2007 |
| WO | 2016040595 A1 | 3/2016 |
| WO | 2016085632 A2 | 6/2016 |

(Continued)

OTHER PUBLICATIONS

Kersting et al, Multiplex isothermal solid-phase recombinase polymerase amplification for the specific and fast DNA-based detection of three bacterial pathogens, Mikrochim Acta. 2014;181(13-14):1715-1723. doi: 10.1007/s00604-014-1198-5. Epub Feb. 18, 2014.*

(Continued)

*Primary Examiner* — Aaron A Priest

(74) *Attorney, Agent, or Firm* — Cantor Colburn, LLP; Samantha Updegraff

(57) ABSTRACT

The present invention is directed to methods and devices for identification of pathogens, and more particularly to solid phase recombinase polymerase amplification (SP-RPA) methods and devices for massively multiplexed solid-phase isothermal identification of human pathogens from patient samples. The principal application for multiplexed solid-phase isothermal identification of human pathogens is point-of-care diagnostics.

20 Claims, 3 Drawing Sheets

Specification includes a Sequence Listing.

DNA primers immobilized on surface and free in solution — Recombinase displaces sample DNA strands and anneals primers — Polymerase synthesizes fluorescent-labeled DNA strands — Wash away unbound fluorescent primer and amplicons — Image fluorescent spots to determine DNA amplification

(56)             References Cited

FOREIGN PATENT DOCUMENTS

| | | | |
|---|---|---|---|
| WO | 2017152122 A2 | 9/2017 | |
| WO | 2017205668 A1 | 11/2017 | |
| WO | WO-2024249061 A1 * | 12/2024 | ........... C12Q 1/6818 |

OTHER PUBLICATIONS

Mayboroda, Development of Diagnostic Platform for Detection of Biological Agents and Toxic Microalgae Using Isothermal Amplification, Doctoral Thesis, 2017, Universitat Rovira I Virgili.*

Sanchez-Salcedo et al, On-Gold Recombinase Polymerase Primer Elongation for Electrochemical Detection of Bacterial Genome: Mechanism Insights and Influencing Factors, ChemElectroChem, vol. 6, Issue3, Feb. 1, 2019, pp. 793-800.*

Kunze et al, On-Chip Isothermal Nucleic Acid Amplification on Flow-Based Chemiluminescence Microarray Analysis Platform for the Detection of Viruses and Bacteria, Anal Chem. Jan. 5, 2016;88(1):898-905. doi: 10.1021/acs.analchem.5b03540. Epub Dec. 11, 2015.*

Berger, J. et al., "Portable pathogen diagnostics using microfluidic cartridges made from continuous liquid interface production additive manufacturing," Anal. Chem. (2021) 93(29):10048-10055.

Lawi, W. et al., "A Microfluidic Cartridge System for Multiplexed Clinical Analysis," JALA Charlottesv VA (2009) 14(6):407-412.

Lobato, I. M. et al., "Recombinase polymerase ampli!cation: Basics, applications and recent advances," Trends in Analytical Chemistry (2018) 98:19-35.

Smith, S. et al., "Microfluidic Cartridges for Automated, Point-of-Care Blood Cell Counting," SLAS Technology (2017) 22(2):176-185.

* cited by examiner

DNA primers immobilized
on surface and free
in solution

Recombinase displaces
sample DNA strands and
anneals primers

Polymerase synthesizes
fluorescent-labeled
DNA strands

Wash away unbound
fluorescent primer
and amplicons

Image fluorescent
spots to determine
DNA amplification

SOLID PHASE RECOMBINASE POLYMERASE AMPLIFICATION FOR HUMAN PATHOGEN IDENTIFICATION

STATEMENT OF GOVERNMENT SUPPORT

This invention was made with Government support under Contract No. DE-NA0003525 awarded by the United States Department of Energy/National Nuclear Security Administration. The U.S. Government has certain rights in the invention.

REFERENCE TO A SEQUENCE LISTING APPENDIX

A sequence listing appendix including an ASCII formatted file accompanies this application. The appendix includes a file named "SD-163450 XML Draft of Sequence List.XML," created on Apr. 3, 2023 (size of 13.6 kilobytes), which is hereby incorporated by reference in its entirety.

BACKGROUND OF THE INVENTION

Field of the Invention

The present invention is directed to methods and devices for identification of pathogens, and more particularly to solid phase recombinase polymerase amplification methods and devices for massively multiplexed solid-phase isothermal identification of human pathogens from patient samples.

Brief Description of the Related Art

Immunodiagnostic detection and molecular sensing are essential for the rapid detection of human pathogens and characterization of antimicrobial properties. This information is critical for the early application of the most applicable therapeutic treatments for infections. Fieldable instrumentation is essential for the assessment of individuals and samples in remote or contested environments that lack the availability or infrastructure for conventional central diagnostic laboratories. Moreover, assays must make use of samples collected by minimally invasive techniques and have easy to interpret results that are rapidly acquired. Furthermore, detection flexibility would include an open-architecture where the detection specifics can be modified for targeting new and changing biological and pathological threats. Thus, the ideal detection platform would have the capability to identify the human pathogen and determine antimicrobial resistance for the most effective therapeutic treatment. Ideally, detection would be performed using a system that can utilize small sample sizes and is isothermal in nature such that complexities of changing temperatures would be alleviated. Recombinase polymerase amplification is one system that possesses these advantages. See, for example, Lobato et al., Trends in Analytical Chemistry 98 (2018) 19e35; U.S. Pat. No. 10,538,760; and U.S. Patent Application Publication 2020/0087709.

Identification of specific infectious diseases is currently performed in a variety of ways known in the art, including chemical and physical assays, and microscopic examinations. See, for example, Berger et al., Anal. Chem. 93 10048-10055 (Jul. 12, 2021); U.S. Pat. No. 10,272,434; International Application WO 2017/205668; International Application WO 2016/040595; International Application WO 2007/096702; International Application WO 2017/152122; and International Application WO 2016/085632.

Although various methods and devices are available for detecting an infectious disease, it is appreciated that there is still a need for a reliable, sensitive, simple, convenient, versatile, and cost-effective method to detect the presence of a disease-causing pathogen in body fluids, food samples, water samples, air samples at the earliest stage possible to prevent the spread of the disease and prevent more serious health harms. There is also a need for a detection device that can be used in clinical, or field setting and requires only minimal training to use. The present invention is believed to be an answer to that need.

SUMMARY OF THE INVENTION

In one embodiment, the present invention is directed to a sample analysis device, comprising: (a) a sample and reagent input module; (b) a multiplex reaction module in communication with the input module, the multiplex reaction module comprising a plurality of sample handling chambers for performing recombinase polymerase amplification assay, wherein the recombinase polymerase amplification assay comprises at least one forward primer immobilized on a solid support and at least one reverse primer comprising a detectable label; wherein the forward primer and the reverse primer are complementary to a target nucleic acid; (c) a data analysis module in communication with the multiplex reaction module, wherein the data analysis module analyzes for the presence of the detectable label; and (d) a waste output module for receiving waste from the data analysis module.

In another embodiment, the present invention is directed to a method of detecting a target nucleic acid in a patient sample, the method comprising the steps of: (a) obtaining a sample from a patient, the sample containing nucleic acid; (b) amplifying the nucleic acid on a multiplex array using a recombinase polymerase amplification (RPA) assay with at least one forward primer and at least one reverse primer, wherein the forward primer is immobilized on a solid support and the reverse primer contains a detectable label; and wherein the forward primer and the reverse primer are complementary to the target nucleic acid; and (c) detecting for the presence of the detectable label on the target nucleic acid.

These and other aspects will be described in the following written description and accompanying drawings.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein.

DETAILED DESCRIPTION OF THE INVENTION

Terminology

Figure 1:
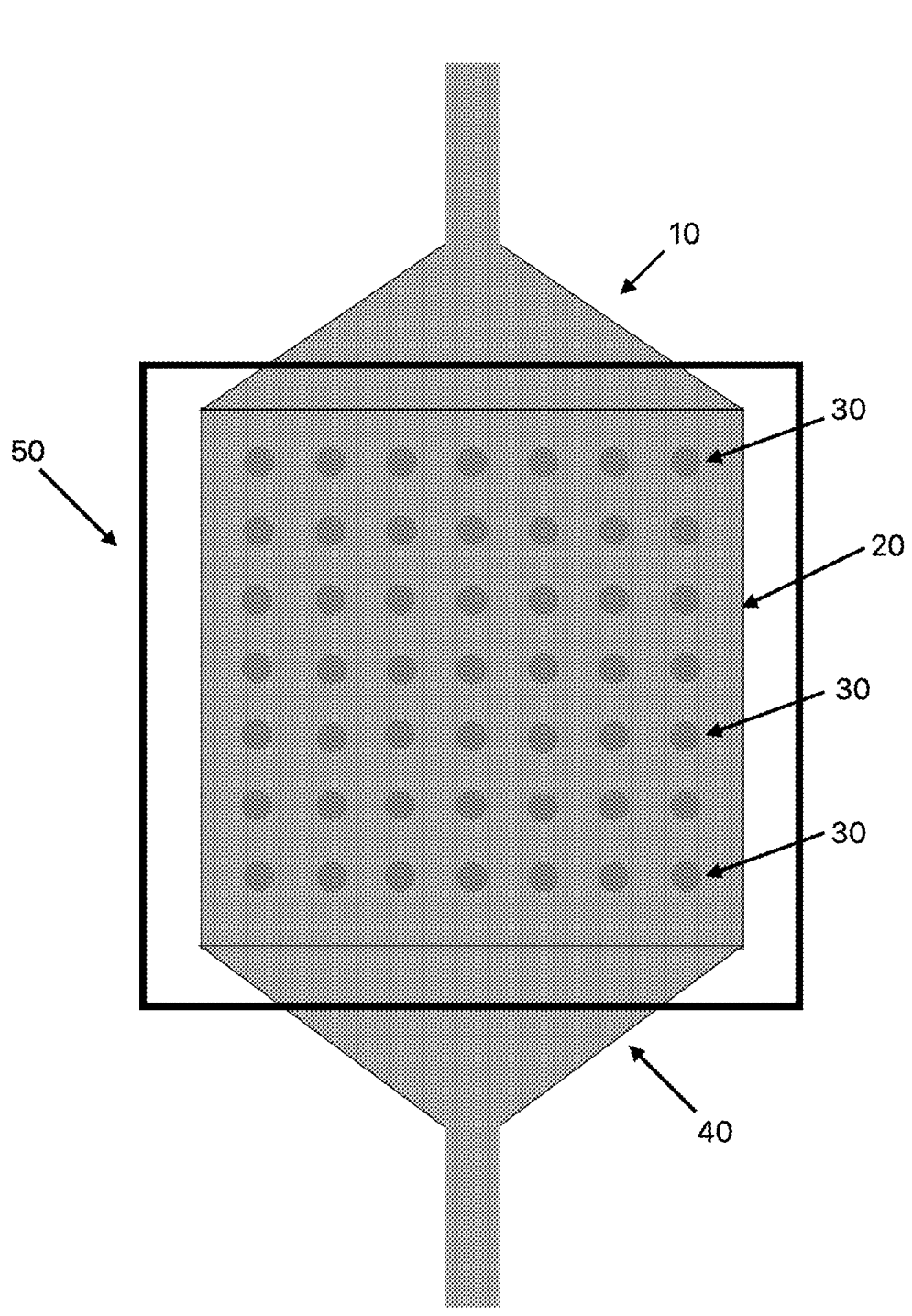
FIG. 1 is a diagram of the device of the invention.

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers and encompass heavy isotopes and radioactive isotopes. By way of general example, and without limitation, isotopes of hydrogen include tritium and deuterium, and isotopes of carbon include 11C, 13C, and 14C. Accordingly, the compounds disclosed herein may include heavy or radioactive isotopes in the structure of the compounds or as substituents attached thereto. Examples of useful heavy or radioactive isotopes include 18F, 15N, 18O, 76Br, 125I and 131I. All formulae disclosed herein include all salts of such Formulae.

The opened ended term "comprising" includes the intermediate and closed terms "consisting essentially of" and "consisting of."

The term "substituted" means that any one or more hydrogens on the designated atom or group is replaced with a selection from the indicated group, provided that the designated atom's normal valence is not exceeded. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent.

"Alkyl" includes both branched and straight chain saturated aliphatic hydrocarbon groups, having the specified number of carbon atoms, generally from 1 to about 15 carbon atoms. The terms $C_{1-6}$ alkyl, $C_1$-$C_6$ alkyl and $C_1$-$C_6$ alkyl as used herein all indicate an alkyl group having from 1, 2, 3, 4, 5, 6 or up to 15 carbon atoms. Other embodiments include alkyl groups having from 1 to 8 carbon atoms, 1 to 4 carbon atoms or 1 or 2 carbon atoms, e.g. $C_{1-8}$ alkyl, $C_{1-4}$ alkyl, and $C_{1-2}$ alkyl. When $C_{0-n}$ alkyl is used herein in conjunction with another group, for example, —$C_{0-4}$ alkyl (phenyl), the indicated group, in this case phenyl, is either directly bound by a single covalent bond ($C_0$ alkyl), or attached by an alkyl chain having the specified number of carbon atoms, in this case 1, 2, 3, or 4 carbon atoms. Alkyls can also be attached via other groups such as heteroatoms as in —$OC_{0-4}$ alkyl($C_{3-7}$ cycloalkyl). Examples of alkyl include, but are not limited to, methyl, ethyl, n-propyl, isopropyl, n-butyl, 3-methylbutyl, t-butyl, n-pentyl, and sec-pentyl.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly, an "alkylthio" or a "thioalkyl" group is an alkyl group as defined above with the indicated number of carbon atoms covalently bound to the group it substitutes by a sulfur bridge (—S—). Similarly, "alkenyloxy", "alkynyloxy", and "cycloalkyloxy" refer to alkenyl, alkynyl, and cycloalkyl groups, in each instance covalently bound to the group it substitutes by an oxygen bridge (—O—).

"Halo" or "halogen" means fluoro, chloro, bromo, or iodo, and are defined herein to include all isotopes of same, including heavy isotopes and radioactive isotopes. Examples of useful halo isotopes include 18F, 76Br, and 131I. Additional isotopes will be readily appreciated by one of skill in the art.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined above attached through an oxygen bridge (oxygen of an alcohol radical).

"Peptide" means a molecule which is a chain of amino acids linked together via amide bonds (also called peptide bonds).

"Pharmaceutical compositions" means compositions comprising at least one active agent, such as a compound or salt of Formula I, and at least one other substance, such as a carrier. Pharmaceutical compositions meet the U.S. FDA's GMP (good manufacturing practice) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

A "patient" means a human or non-human animal in need of medical treatment. Medical treatment can include treatment of an existing condition, such as a disease or disorder or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any disease symptom, slow disease progression or cause disease regression. In certain embodiments, treatment of the disease may be commenced before the patient presents symptoms of the disease.

A "therapeutically effective amount" of a pharmaceutical composition means an amount effective, when administered to a patient, to provide a therapeutic benefit such as an amelioration of symptoms, decrease disease progression, or cause disease regression.

A "therapeutic compound" means a compound which can be used for diagnosis or treatment of a disease. The compounds can be small molecules, peptides, proteins, or other kinds of molecules.

A significant change is any detectable change that is statistically significant in a standard parametric test of statistical significance such as Student's T-test, where $p<0.05$.

As indicated above, the present invention is directed to a device and method for massively multiplexed solid-phase isothermal identification of human pathogens from patient samples. The device of the present invention combines isothermal recombinase polymerase amplification (RPA) with a two-dimensional printed array of DNA primers for speciation. The term "multiplexed" and "massively multiplexed" means thousands of reaction spots or wells designated as reaction chambers on a single substrate or device, for example 2-16 reaction wells or spots per square millimeter, or approximately 30,000 wells or spots per a standard 75×25 mm microscope slide. "Multiplex" and "multiplexed" as defined herein means more than one signal, reaction spot or well. "Massively multiplexed" as defined herein means significantly more than one (e.g., 10, 100, or 1000) signal, reaction spot or well. A "massively multiplexed array" means an ordered array of multiplexed or massively multiplexed reaction spots or wells. A "multiplex reaction module" as defined herein is a module, device, or substrate that utilizes a massively multiplexed array of reaction spots or wells.

As indicated above and as shown in FIG. 1, the sample analysis device of the invention includes a sample and reagent input module 10, a multiplex reaction module 20 in fluid communication with the input module 10 and containing an array of sample handling chambers 30, a data analysis module 50 in communication with the multiplex reaction module 20, wherein the data analysis module 50 analyzes for the presence of a detectable label; and a waste output module 40 for receiving waste from the data analysis module 20. Each of these components is described in more detail below.

The target nucleic acid is preferably a nucleic acid or nucleotide sequence from a pathogen, where the biological sample contains or is suspected of containing the pathogen. Accordingly, the methods provided herein are useful to detect any pathogen or infectious agent. Pathogens and infectious agents may comprise viruses, (e.g., single stranded RNA viruses, single stranded DNA viruses, Zika virus, HIV, hepatitis A, B, and C virus, HSV, CMV EBV, HPV), parasites (e.g., protozoan and metazoan pathogens such as *Plasmodia* species, *Leishmania* species, *Schistosoma* species, *Trypanosoma* species), bacteria (e.g., Mycobacteria, in particular, *M. tuberculosis, Salmonella*, Streptococci, *E. coli*, Staphylococci), fungi (e.g., *Candida* species, *Aspergillus* species), *Pneumocystis carinii*, and prions. In certain embodiments, the pathogen is a virus, and the methods can be used to detect any virus or infection. In other embodiments, the pathogens that are detected are bacteria, fungi, or parasites. An advantage of the methods and systems described herein is that they can be applied for the detection and identification of essentially any nucleic acid-containing organism. Accordingly, the pathogen or infectious agent can be virtually any pathogen or infectious agent for which genetic information (e.g., gene sequences) is available. In other cases, the target nucleic acid is human in origin. In such cases, the methods can be employed to detect one or more target nucleic acids in a biological sample such as a biological sample obtained for forensic analysis, for genotyping, and the like.

Target nucleic acids or nucleotide sequences may also include, without limitation, antibiotic resistance genes or other acquired genes or mutations; DNA or RNA sequences that can identify a species (e.g., ribosomal RNAs or DNAs); DNA or RNA sequences that are associated with a particular genetic condition (e.g., where the target comprises a single nucleotide polymorphism (SNP) for which PAM identification is advantageous, including, without limitation, BRCA1/BRCA2 mutations, cystic fibrosis, Duchenne muscular dystrophy, hemochromatosis); DNA or RNA sequences for identifying a particular person with high certainty (e.g., identifying a suspect in a criminal investigation; identifying a "high value target" in an operation). It will be appreciated that SNPs can also be used with genome-wide association studies (GWAS) data for determining potential of genetic disease or for individual or subpopulation profiling.

For forensic applications, the target nucleotide sequence can be a DNA or RNA sequence associated with one or more particular identifiable features (e.g., skin color, hair color, eye color). In such cases, a biological sample can be assayed to detect a target nucleic acid of an unknown subject or for comparison to samples from known individuals. For applications related to pathogen detection, detection of particular RNA sequences is advantageous for determining, for example, the life cycle stage of a pathogen associated with an infection. By way of example, particular target nucleic acids can be detected to detect the presence of malaria parasite *Plasmodium falciparum* and to determine whether the parasite is in a life cycle phase in which it can reproduce and, thus, transmit infection. Other applications for which the methods provided herein include, without limitation, profiling species in an environment (e.g., water); profiling species in an human or animal microbiome; food safety applications (e.g., detecting the presence of a pathogenic species, determining or confirming food source/origin such as type of animal or crop plant); obtaining patient expression profiles (e.g., detecting expression of a gene or panel of genes (e.g., biomarkers) to monitor the patient's response to a therapeutic regimen, to select a therapeutic regimen suitable for the patient, or to detect exposure of the patient to a toxin or environmental agent that affects expression of the gene or panel of genes); and molecular encryption applications such as marking certain products (e.g., high value products) using nucleic acid barcodes.

The nucleic acid molecule can be, e.g., an RNA, a DNA, an mRNA, and/or a genomic nucleic acid. In some embodiments of any of the aspects, the nucleic acid molecule can be human, animal, prokaryotic, eukaryotic, or pathogenic in origin. In some embodiments of any of the aspects, the nucleic acid molecule can be of viral origin. Nucleic acids and/or other moieties of the invention may be isolated. As used herein, "isolated" means separate from at least some of the components with which it is usually associated whether it is derived from a naturally occurring source or made synthetically, in whole or in part.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

Biological samples appropriate for use according to the methods provided herein include, without limitation, blood, serum, urine, saliva, tissues, cells, and organs, or portions thereof, as well as purified or partially purified nucleic acids and surface swabs containing the aforementioned samples.

The sample analysis device of the invention generally can take any form, for example simple microscope slides or complex reaction cartridges that are generally known in the art. In one preferred embodiment, the sample device of the invention is a cartridge-based device containing microfluidic fluid handling systems, electronic systems, and reaction chambers for encapsulated flow, throughput, detection, and automation of sample analysis as described in U.S. Pat. No. 10,272,434.

The multiplex reaction module 20 includes a plurality of sample handling chambers 30 in a two-dimensional array for performing massively multiplexed recombinase polymerase amplification assays (described in more detail below). Within each sample handling chamber 30 there are numerous wells or spots that correspond to individual nucleic acid target sequences. The number of wells or spots can range from 2, 4, 8, 16, or more wells or spots per square millimeter, or upwards of 30,000 wells or spots per a standard 75×25 mm microscope slide. In one embodiment, 400 wells or spots are utilized (e.g. 20×20) per square millimeter.

Each sample handling chamber has a volume ranging from 1 μL to 500 μL, and preferably 5 μL to 100 μL and is suitable for performing multiplexed recombinase polymerase assays (RPA) that are generally known in the art. Volume will depend on the number of wells or dots per chamber and the potential for adequate mixing (especially for higher volumes). The substrate of the multiplex reaction module may be functionalized with an agent such as epoxy silane that permits attachment (for example via covalent or ionic bonding) of a nucleic acid primer that is utilized in the recombinase polymerase amplification reactions described below. In one embodiment, glass surfaces in the multiplex reaction module 20 are functionalized with epoxy silane for the attachment of amino-modified DNA primers to promote recombinase polymerase reaction on the glass surface. The immobilized DNA is patterned with specific sequences corresponding to specific species that are physically separated and located on the glass surface.

A sample and reagent input module 10 is in fluid communication with the multiplex reaction module 20 so that samples and reagents may be added to the reaction module. The reagents utilized in the device and method of the invention are those appropriate for the RPA reaction, and include buffers, DNA binding proteins, free nucleotides, additional primers, and the like, as well as at least one forward nucleic acid primer that will be immobilized in solid support in the reaction module and at least one reverse nucleic acid primer comprising a detectable label such as a fluorescent label, radioactive label, chemiluminescence label, electron spin resonance label, and the like, that is detectable by the data analysis module 50. A waste output module 40 collects waste from the device.

The data analysis module 50 is in communication with the multiplex reaction module and allows for detection of a signal at a predefined position in the multiplex reaction module 20. The data analysis module can be any detection device but is preferably chosen to detect the detectable label on the reverse nucleic acid primer. Suitable data analysis modules include components that can detect and quantify labels such as radioactive atoms such as 18F, 1251, 14C, 3H and the like, chemiluminescence, electron spin resonance, or fluorescence emitted from the detectable label.

The device of the invention may be fabricated using conventional techniques such as micromanufacturing, 3D printing, and the like.

The principal application space for multiplexed solid-phase isothermal identification of human pathogens includes but is not limited to point-of-care diagnostics. Specifically, the identification of unknown infections or pathogens within clinician offices or in remote locations without central diagnostic testing facilities available. The technology is highly flexible and in addition to the uses outlined above can be retargeted to identify the presence of human and non-human pathogens as well as other speciation activities that would include determining species of plant, animal, fungi, protist, and bacteria in the field. The species targets can also be replaced with specific genes-of-interest that would include antibiotic resistance and toxin genes.

EXAMPLES

Example 1

Forward and reverse DNA primers were designed to target unique DNA sequences in the glyceraldehyde 3-phosphate dehydrogenase (GAPDH) gene for the specific amplification of a single target species (Table 1). It will be appreciated that while DNA sequences of GAPDH were used here, other housekeeping genes such as actin, 18S rRNA, ubiquitin, antibiotic resistance genes, toxin genes, CRISPR genes, SNPs and genetic rearrangements could also be used.

TABLE 1

| DNA Primer Sequences | | | | |
|---|---|---|---|---|
| Species | Name | Sequence | Modification | SEQ ID NO. |
| E. coli | ecoGAPDH-f | tttttttttttttttttACATGATTCAAACTACGGACC | /5AmMC12/ | SEQ ID NO: 1 |
| | ecoGAPDH-r | ATCCAGAGTGTCGTCATTGAC | /55-TAMK/ | SEQ ID NO: 2 |

TABLE 1-continued

DNA Primer Sequences

| Species | Name | Sequence | Modification | SEQ ID NO. |
|---------|------|----------|--------------|------------|
| K. pneumoniae | kpnGAPD H-f | tttttttttttttttTGTTAC GTCGTTTATTAGAAGTCGAC | /5AmMC1 2/ | SEQ ID NO: 3 |
| | kpnGAPD H-r | TTCTCCAGCACCGATACCAG | /55-TAMK/ | SEQ ID NO: 4 |
| P. aeruginosa | paeGAPD H-f | tttttttttttttttTATCCG CCTGGCCATCAAC | /5AmMC1 2/ | SEQ ID NO: 5 |
| | paeGAPD H-r | TACACGTCGGAGAGGTTCTGG | /55-TAMK/ | SEQ ID NO: 6 |
| E. faecium | efaeGAP DH-f | tttttttttttttttAGCAAT CAACGACTTAACAAGTCC | /5AmMC1 2/ | SEQ ID NO: 7 |
| | efaeGAP DH-r | GCCTCTTACTGGTCCATCTAAC | /55-TAMK/ | SEQ ID NO: 8 |
| S. aureus | sauGAPD H-f | tttttttttttttttTGGTGAT GCTGATAATAGTCAATC | /5AmMC1 2/ | SEQ ID NO: 9 |
| | sauGAPD H-r | TGTTTATGACTGATGGCTCTAA CAAC | /55-TAMK/ | SEQ ID NO: 10 |
| N. gonorrhoeae | ngoGAPD H-f | tttttttttttttttAGGCATC GGACTTTATTTCACAACCGGGA GAC | /5AmMC1 2/ | SEQ ID NO: 11 |
| | ngoGAPD H-r | CGGCGGAAATGACAGTTTCGCT ACCGTCCAAG | /55-TAMK/ | SEQ ID NO: 12 |

Figure 2:
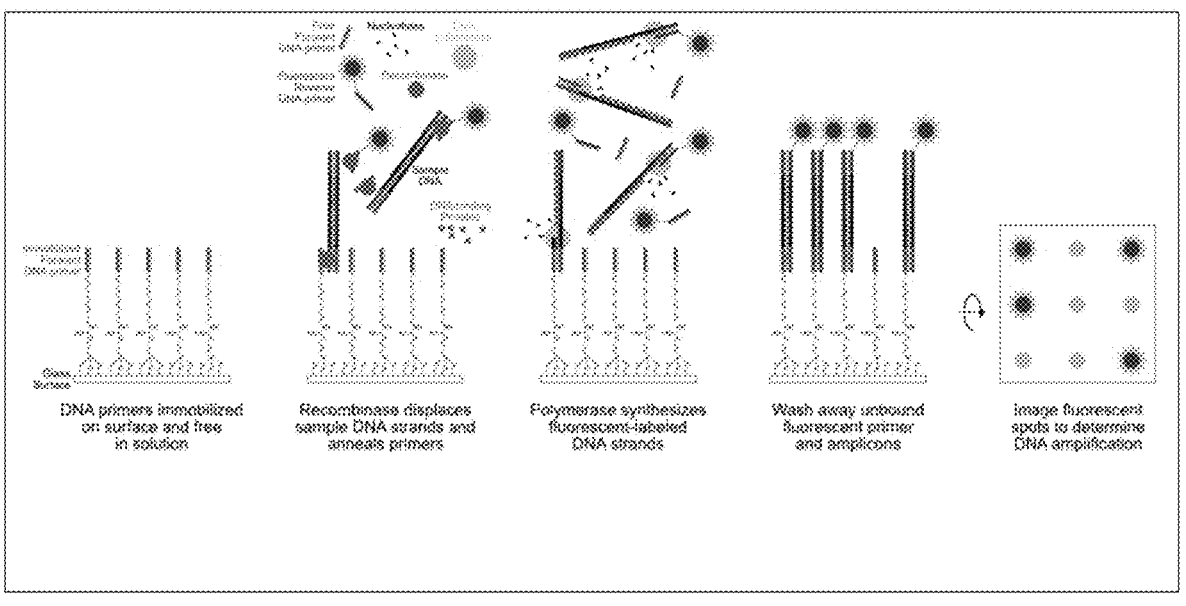
FIG. 2 is a diagram of the method of the invention illustrating multiplexed solid-phase isothermal identification of human pathogens.

The forward DNA primers were appended with either a 5'-amine or 5'-thiol for covalent or coordinate bonding to silanizated or gold coated glass, respectively. Additionally, the forward primer has a 15-nt poly-thymine (15-dT) tract located between the 5'-amine or 5'-thiol and the GAPDH priming region sequence. This 15-nt tract facilitates a stand-off distance from the glass surface. For visualization, the reverse DNA primers are appended with 5-TAMRA fluorophores that are excited with 546 nm and emission of 579 nm. A species presence is detected by fluorescence signals at the predefined position in DNA patterned array shown in FIG. 2. Primer concentrations and wash conditions were optimized as follows.

Silica microscope slides (75 mm×25 mm) are rinsed with acetone, methanol, isopropanol, and water, in that order before drying. The slides are dried with nitrogen gas and placed into a UV/ozone Plasma Cleaner (UVOCS) for 15 min, exposed to 1% (3-glycidoxypropylmethyl)diethoxysilane in toluene for 15 min followed by a brief soak in the pure toluene, immediately dried with nitrogen gas and placed in an oven at 120° C. for 30 min. The slides were allowed to cool to room temperature and 50 μM amine-modified DNA primer in 1× phosphate buffer saline are printed with an SpotBot 2 Microarray Printer (ArrayIt Corp., Sunnyvale, CA) in the presence of 60-70% relative humidity and incubated overnight. DNA printed slides are stored under low vacuum until used. Reaction chambers are formed by applying SecureSeal Hybridization Chambers (Grace Bio Labs, Bend, OR) to the slide and the surface blocked with 0.01% BSA in 0.1×PBS for 2 hours and then rinsed with water. Immediately after aspirating the water, the Recombinase Polymerase Amplification (TwistDx Ltd, United Kingdom) reaction was added by comprising 1× Reaction buffer, 1× Basic E-mix, 1× Core Reaction Mix, 400 μM each dNTP, 480 nM forward and reverse primer. To initiate the reaction, 14.5 mM MgOAc and DNA template are added, mixed, and then transferred to the reaction chamber with the printed DNA. A spot and pitch of ~250 μm allows for a theoretical maximum of 16 spots per square mm, 1600 spots per square cm, and 30,000 spots per a standard microscope slide measuring 75×25 mm.

Figure 3:
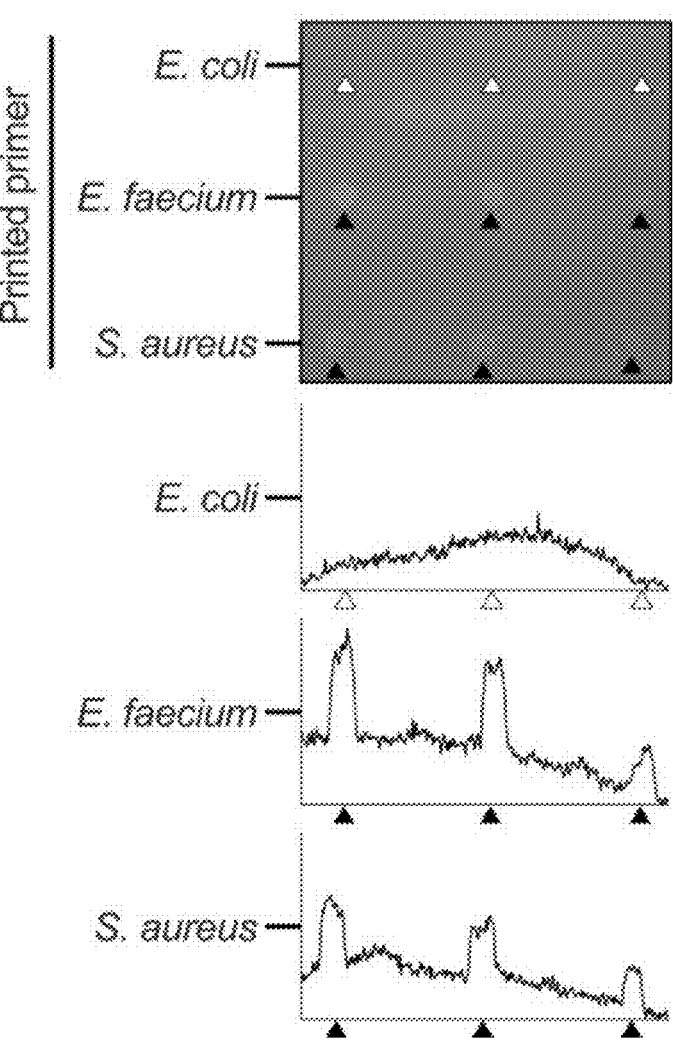
FIG. 3 is a diagram showing identification of human pathogens.

FIG. 3 shows an example of the massively multiplexed solid-phase isothermal identification device of the invention with human pathogens from patient samples. The top image was captured in dry conditions using an Olympus IX70 microscope with a HB2-RFL-T3 light source, TRITC filter cube, 4× magnification, and 8 second exposure.

As shown in FIG. 3, DNA primer specificity and lack of cross-reactivity for the GAPDH protein gene from E. coli, E. faecium, and S. aureus were initially validated by conventional thermocycled PCR, followed by liquid phase conventional isothermal RPA. Identical primer sequences to the thermocycled PCR and liquid phase RPA were appended with the 5'-amine and 15-dT tract. A glass slide was functionalized with epoxy silane for covalent attachment of the 5'-amine DNA forward primer. The DNA forward primer was spotted in triplicate onto the silanizated glass surface. The liquid phase RPA reaction was modified to reduce the in solution forward primer concentration from 480 nM to 96 nM to promote amplicon formation on the immobilized DNA forward primers on the glass surface. Following 20 min at 37° C., the glass slide was washed with 0.2× saline sodium citrate supplemented with 0.1% sodium dodecyl sulfate before imaging. The intensity trace was generated in ImageJ (NIH). There was no signal for the lack of E. coli, yet signal for the present E. faecium and S. aureus genomic DNA, indicating their presence.

All publications, including but not limited to patents and patent applications, cited in this specification are herein incorporated by reference as though set forth in their entirety in the present application.

What is claimed is:

1. A sample analysis device, comprising:

(a) a sample and reagent input module;

(b) a multiplex reaction module in communication with the input module, the multiplex reaction module comprising a plurality of sample handling chambers for performing recombinase polymerase amplification assay, wherein the recombinase polymerase amplification assay comprises at least one forward primer immobilized on a solid support and at least one reverse primer comprising a detectable label; wherein the forward primer and the reverse primer are complementary to a target nucleic acid;

wherein the at least one forward primer is selected from the group consisting of SEQ ID NO:1, SEQ ID NO:3, SEQ ID NO:5, SEQ ID NO:7, SEQ ID NO:9, and SEQ ID NO:11; and wherein the at least one reverse primer is selected from the group consisting of SEQ ID NO:2, SEQ ID NO:4, SEQ ID NO:6, SEQ ID NO:8, SEQ ID NO:10, and SEQ ID NO:12:

(c) a data analysis module in communication with the multiplex reaction module, wherein the data analysis module analyzes for the presence of the detectable label; and (d) a waste output module for receiving waste from the data analysis module.

2. The sample analysis device of claim 1, wherein the plurality of sample handling chambers in the multiplex reaction module comprise 2-500 reaction wells or spots per square millimeter.

3. The sample analysis device of claim 2, wherein the plurality of sample handling chambers in the multiplex reaction module comprise approximately 400 reaction wells or spots per square millimeter.

4. The sample analysis device of claim 1, wherein the plurality of sample handling chambers in the multiplex reaction module comprise approximately 30,000 wells or spots per microscope slide.

5. The sample analysis device of claim 1, wherein the plurality of sample handling chambers in the multiplex reaction module are arranged in a two-dimensional printed array.

6. The sample analysis device of claim 1, wherein said target nucleic acid comprises a nucleic acid or nucleotide sequence from a pathogen.

7. The sample analysis device of claim 6, wherein said pathogen is a virus, parasite, bacteria, fungi, and combinations thereof.

8. The sample analysis device of claim 7, wherein the pathogen is selected from single stranded RNA viruses, single stranded DNA viruses, Zika virus, HIV, hepatitis A, B, and C virus, HSV, CMV EBV, HPV, *Plasmodia* species, *Leishmania* species, *Schistosoma* species, *Trypanosoma* species, mycobacteria, *Salmonella*, Streptococci, *E. coli*, Staphylococci, *Candida, Aspergillus, Pneumocystis carinii*, prions, and combinations thereof.

9. The sample analysis device of claim 1, wherein said target nucleic acid is selected from ribosomal RNAs or DNAs, DNA or RNA sequences that are associated with a genetic condition; DNA or RNA sequences for identifying a person; DNA or RNA sequences containing single nucleotide polymorphisms, and combinations thereof.

10. The sample analysis device of claim 1, wherein said sample handling chambers each have a volume ranging from 1 μL to 500 μL.

11. The sample analysis device of claim 1, wherein said multiplex reaction module comprises a glass substrate that is functionalized with epoxy silane.

12. The sample analysis device of claim 1, wherein said detectable label is selected from a fluorescent label, a radioactive label, a chemiluminescence label, an electron spin resonance label, and combinations thereof.

13. The sample analysis device of claim 1, wherein said data analysis modules detects radioactive labels, fluorescent labels, chemiluminescent labels, electron spin labels, and combinations thereof.

14. The sample analysis device of claim 1, wherein said forward primer and said reverse primer are each complementary to the glyceraldehyde 3-phosphate dehydrogenase (GAPDH), actin, 18S rRNA, ubiquitin, antibiotic resistance genes, toxin genes, CRISPR genes, SNPs, and combinations thereof.

15. A method of detecting a target nucleic acid in a patient sample, the method comprising the steps of:
  (a) obtaining a sample from a patient, the sample containing nucleic acid;
  (b) amplifying the nucleic acid on a multiplex array using a recombinase polymerase amplification (RPA) assay with at least one forward primer and at least one reverse primer, wherein the forward primer is immobilized on a solid support and the reverse primer contains a detectable label; and wherein the forward primer and the reverse primer are complementary to the target nucleic acid;
  wherein the at least one forward primer is selected from the group consisting of SEQ ID NO:1, SEQ ID NO:3, SEQ ID NO:5, SEQ ID NO:7, SEQ ID NO:9, and SEQ ID NO:11; and
  wherein the at least one reverse primer is selected from the group consisting of SEQ ID NO:2, SEQ ID NO:4, SEQ ID NO:6, SEQ ID NO:8, SEQ ID NO:10, and SEQ ID NO:12; and (c) detecting for the presence of the detectable label on the target nucleic acid.

16. The method of claim 15, wherein the sample is selected from blood, serum, urine, saliva, tissues, cells, and organs, purified or partially purified nucleic acids, or portions thereof.

17. The method of claim 15 wherein the nucleic acid is a nucleic acid from a pathogen.

18. The method of claim 17, wherein the pathogen is a virus, parasite, bacteria, fungi, and combinations thereof.

19. The method of claim 17 wherein the pathogen is selected from single stranded RNA viruses, single stranded DNA viruses, Zika virus, HIV, hepatitis A, B, and C virus, HSV, CMV EBV, HPV, *Plasmodia* species, *Leishmania* species, *Schistosoma* species, *Trypanosoma* species, mycobacteria, *Salmonella*, Streptococci, *E. coli*, Staphylococci, *Candida, Aspergillus, Pneumocystis carinii*, prions, and combinations thereof.

20. The method of claim 15, wherein said forward primer and said reverse primer are each complementary to the glyceraldehyde 3-phosphate dehydrogenase (GAPDH), actin, 18S rRNA, ubiquitin, antibiotic resistance genes, toxin genes, CRISPR genes, SNPs, and combinations thereof.

\* \* \* \* \*

SEQUENCE LISTING

Sequence total quantity: 12
SEQ ID NO: 1              moltype = DNA   length = 36
FEATURE                   Location/Qualifiers
source                    1..36
                          mol_type = genomic DNA
                          note = ecoGAPDH-f; Modification /5AmMC12/
                          organism = Escherichia coli
SEQUENCE: 1
tttttttttt tttttacatg attcaaacta cggacc                              36

SEQ ID NO: 2              moltype = DNA   length = 21
FEATURE                   Location/Qualifiers
source                    1..21
                          mol_type = genomic DNA
                          note = ecoGAPDH-r; Modification /55-TAMK/
                          organism = Escherichia coli
SEQUENCE: 2
atccagagtg tcgtcattga c                                              21

SEQ ID NO: 3              moltype = DNA   length = 41
FEATURE                   Location/Qualifiers
source                    1..41
                          mol_type = genomic DNA
                          note = kpnGAPDH-f; Modification /5AmMC12/
                          organism = Klebsiella pneumoniae
SEQUENCE: 3
tttttttttt tttttgtta cgtcgtttat tagaagtcga c                         41

SEQ ID NO: 4              moltype = DNA   length = 20
FEATURE                   Location/Qualifiers
source                    1..20
                          mol_type = genomic DNA
                          note = kpnGAPDH-r; Modification /55-TAMK/
                          organism = Klebsiella pneumoniae
SEQUENCE: 4
ttctccagca ccgataccag                                                20

SEQ ID NO: 5              moltype = DNA   length = 34
FEATURE                   Location/Qualifiers
source                    1..34
                          mol_type = genomic DNA
                          note = paeGAPDH-f; Modification /5AmMC12/
                          organism = Pseudomonas aeruginosa
SEQUENCE: 5
tttttttttt tttttatcc gcctggccat caac                                 34

SEQ ID NO: 6              moltype = DNA   length = 21
FEATURE                   Location/Qualifiers
source                    1..21
                          mol_type = genomic DNA
                          note = paeGAPDH-r; Modification /55-TAMK/
                          organism = Pseudomonas aeruginosa
SEQUENCE: 6
tacacgtcgg agaggttctg g                                              21

SEQ ID NO: 7              moltype = DNA   length = 39
FEATURE                   Location/Qualifiers
source                    1..39
                          mol_type = genomic DNA
                          note = efaeGAPDH-f; Modification /5AmMC12/
                          organism = Enterococcus faecium
SEQUENCE: 7
tttttttttt tttttagcaa tcaacgactt aacaagtcc                           39

SEQ ID NO: 8              moltype = DNA   length = 22
FEATURE                   Location/Qualifiers
source                    1..22
                          mol_type = genomic DNA
                          note = efaeGAPDH-r; Modification /55TAMK/
                          organism = Enterococcus faecium
SEQUENCE: 8
gcctcttact ggtccatcta ac                                             22

SEQ ID NO: 9              moltype = DNA   length = 39
FEATURE                   Location/Qualifiers
source                    1..39
                          mol_type = genomic DNA
                          note = sauGAPDH-f; Modification /5AmMC12/

-continued

```
                        organism = Staphylococcus aureus
SEQUENCE: 9
tttttttttt tttttttggtg atgctgataa tagtcaatc                        39

SEQ ID NO: 10          moltype = DNA   length = 26
FEATURE                Location/Qualifiers
source                 1..26
                       mol_type = genomic DNA
                       note = sauGAPDH-r; Modification /55-TAMK/
                       organism = Staphylococcus aureus
SEQUENCE: 10
tgtttatgac tgatggctct aacaac                                       26

SEQ ID NO: 11          moltype = DNA   length = 47
FEATURE                Location/Qualifiers
source                 1..47
                       mol_type = genomic DNA
                       note = ngoGAPDH-f
                       organism = Neisseria gonorrhoeae
SEQUENCE: 11
tttttttttt tttttaggca tcggacttta tttcacaacc gggagac                47

SEQ ID NO: 12          moltype = DNA   length = 32
FEATURE                Location/Qualifiers
source                 1..32
                       mol_type = genomic DNA
                       note = ngoGAPDH-r; Modification /55-TAMK/
                       organism = Neisseria gonorrhoeae
SEQUENCE: 12
cggcggaaat gacagtttcg ctaccgtcca ag                                32
```